United States Patent
Dai et al.

(10) Patent No.: US 7,019,151 B2
(45) Date of Patent: Mar. 28, 2006

(54) TRIPTOLIDE DERIVATIVES AS IMMUNOMODULATORS AND ANTICANCER AGENTS

(75) Inventors: Dongcheng Dai, Mountain View, CA (US); John H. Musser, San Carlos, CA (US)

(73) Assignee: Pharmagenesis, Inc., Palo Alto, CA (US)

( * ) Notice: Subject to any disclaimer, the term of this patent is extended or adjusted under 35 U.S.C. 154(b) by 168 days.

(21) Appl. No.: 10/738,753

(22) Filed: Dec. 16, 2003

(65) Prior Publication Data
US 2004/0152767 A1 Aug. 5, 2004

Related U.S. Application Data

(60) Provisional application No. 60/434,203, filed on Dec. 17, 2002.

(51) Int. Cl.
*C07D 307/93* (2006.01)
(52) U.S. Cl. .................................. 549/298; 549/300
(58) Field of Classification Search ............... 549/298, 549/300
See application file for complete search history.

(56) References Cited

U.S. PATENT DOCUMENTS

| 5,430,054 A | * | 7/1995 | Qian et al. ................ 514/468 |
| 5,663,335 A | | 9/1997 | Qi et al. |
| 6,004,999 A | * | 12/1999 | Jung et al. ................ 514/468 |
| 6,150,539 A | | 11/2000 | Musser |
| 6,620,843 B1 | | 9/2003 | Fidler et al. |

OTHER PUBLICATIONS

Copy of International Search Report in PCT/US2003/040104, published on Jul. 15, 2004 as WO 2004/058246 A1.

* cited by examiner

*Primary Examiner*—Kamal A. Saeed
*Assistant Examiner*—Michael P. Parker
(74) *Attorney, Agent, or Firm*—LeeAnn Gorthey; Perkins Coie LLP

(57) ABSTRACT

Compounds having the structure I:

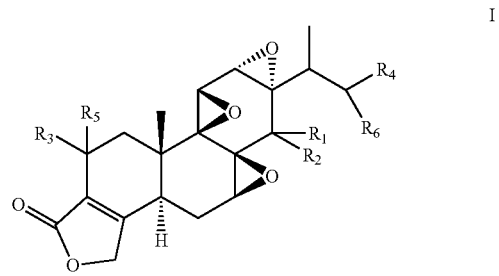

are useful for inducing cell death (apoptosis) and in immunosuppression. In structure I, $R^1$ is H or R, R being selected from lower alkyl, alkenyl, alkynyl, and allenyl, or, $R^1$ together with $R^2$=O (oxo); $R^2$=OH, or, $R^1$ and $R^2$ together=O (oxo); $CR^3R^5$ and $CR^4R^6$ are selected from $CH_2$, CHOH and CROH; at least one of $R^1$, $R^5$ and $R^6$ is R; and at least one of $CR^3R^5$ and $CR^4R^6$ is $CH_2$.

8 Claims, 2 Drawing Sheets

TRIPTOLIDE DERIVATIVES AS IMMUNOMODULATORS AND ANTICANCER AGENTS

This application claims priority to U.S. Provisional Application No. 60/434,203, filed Dec. 17, 2002, which is incorporated in its entirety herein by reference.

FIELD OF THE INVENTION

The present invention relates to compounds useful as immunosuppressive, anti-inflammatory and anticancer agents.

REFERENCES

Gleichmann, E. et al., *Immunol. Today* 5:324 (1984).
Jung, M. J. et al, U.S. Pat. No. 5,972,998 (1999).
Jung, M. J. et al, U.S. Pat. No. 6,004,999 (1999).
Korngold, R. and Sprent, J., *J. Exp. Med.* 148:1687 (1978).
Kupchan, S. M. et. al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al., *J. Chin. Pharm. Sci.* 1:12 (1992).
Murase, N. et al., *Transplantation* 55:701 (1993).
Ono and Lindsey, *J. Thor. Cardiovasc. Surg.* 57(2):225–29 (1969).
Panchagnula, R. and Thomas, N. S., *Intl J of Pharmaceutics* 201(2):131–150 (2000).
Pu, L. et al., *Zhongguo Yaoli Xuebao* 11:76 (1990).
Qi, Y. et al, U.S. Pat. No. 5,663,335 (1997).
Qi, Y. et al, U.S. Pat. No. 5,962,516 (1999).
Wang, J. and Morris, R. E., *Transplantation Proc.* 23:699 (1991).

BACKGROUND OF THE INVENTION

Immunosuppressive agents are widely used in the treatment of autoimmune disease and in treating or preventing transplantation rejection, including the treatment of graft-versus-host disease (GVHD). Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds derived from the Chinese medicinal plant *Tripterygium wilfordii* (TW) have been identified as having immunosuppressive activity, e.g. in the treatment of autoimmune disease, and in treating or preventing transplantation rejection, including the treatment of graft-versus-host disease (GVHD), a condition in which transplanted marrow cells attack the recipient's cells. See, for example, co-owned U.S. Pat. No. 6,150,539 (Triptolide prodrugs having high aqueous solubility), U.S. Pat. No. 5,962,516 (Immunosuppressive compounds and methods), U.S. Pat. No. 5,843,452 (Immunotherapy composition and method), U.S. Pat. No. 5,759,550 (Method for suppressing xenograft rejection), U.S. Pat. No. 5,663,335 (Immunosuppressive compounds and methods), and U.S. Pat. No. 5,648,376 (Immunosuppressant diterpene compound), and references cited therein. Such compounds have also been reported to show anticancer activity. See, for example, Kupchan et al., 1972, 1977, as well as copending and co-owned U.S. application Ser. No. 09/766,156, filed Jan. 19, 2001 and published as U.S. Appn. No. 2002/99051 on Jul. 25, 2002, which is hereby incorporated by reference.

SUMMARY OF THE INVENTION

In one aspect, the invention provides compounds which are useful for immunosuppressive, anti-inflammatory and anticancer therapy. The compounds are derivatives of triptolide represented by Formula I:

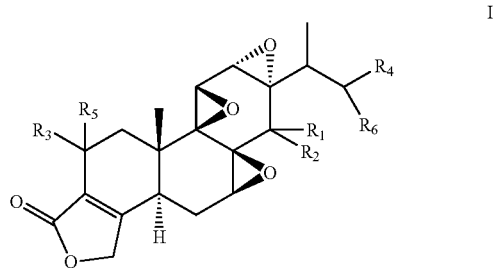

where:
$R^1$ is H or R, where R is selected from lower alkyl, alkenyl, alkynyl, and allenyl, or $R^1$ together with $R^2$=O (oxo);
$R^2$=OH or together with $R^1$=O (oxo);
$CR^3R^5$ and $CR^4R^6$ are selected from $CH_2$, CHOH and CROH;
at least one of $R^1$, $R^5$ and $R^6$ is R; and
at least one of $CR^3R^5$ and $CR^4R^6$ is $CH_2$.

In selected embodiments, R is selected from methyl, allyl, and 2-propynyl; in one embodiment, R is methyl. In one embodiment, which includes C2- or C16-modified triptonides, $R^1$ together with $R^2$=oxo, one of $CR^3R^5$ and $CR^4R^6$ is CROH, and the other is $CH_2$. In another embodiment, which includes C2- or C16-modified triptolides, $R^1$ is H, $R^2$ is OH, one of $CR^3R^5$ and $CR^4R^6$ is CROH, and the other is $CH_2$.

In a further embodiment, which includes C14-modified triptolides, $R^1$ is R and $R^2$ is OH. Such a compound may also be modified either at C2 or at C16; in one embodiment, neither of these sites is modified; i.e. each of $CR^3R^5$ and $CR^4R^6$ is $CH_2$. When R is methyl, this embodiment includes the compound designated herein as PG670.

In another aspect, the invention provides a method of effecting immunosuppression, comprising administering to a subject in need of such treatment, in a pharmaceutically acceptable vehicle, an effective amount of a compound having the structure I as described above, including any of the specific embodiments described above. The invention also provides a method of inducing apoptosis in a cell, by contacting the cell with an effective amount of a compound having the structure I as described above, including any of the specific embodiments described above. In particular, the compound may be the compound designated herein as PG670.

These and other objects and features of the invention will become more fully apparent when the following detailed description of the invention is read in conjunction with the accompanying drawings.

DETAILED DESCRIPTION OF THE INVENTION

I. Definitions

Figure 1:
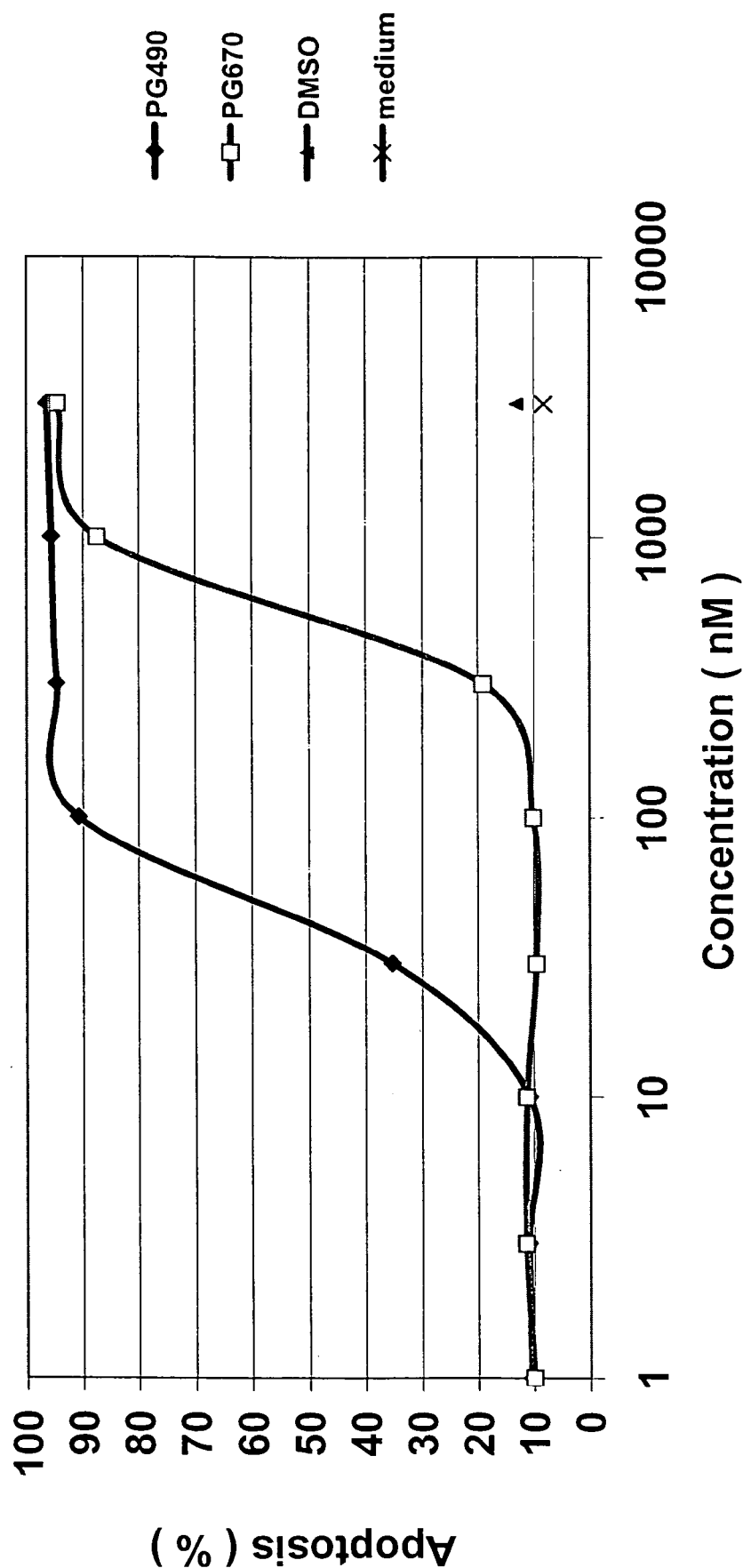
FIG. 1 shows dose-dependent induction of apoptosis in Jurkat cells by a compound of the invention (PG670), in comparison with triptolide (Example 2B)

The terms below have the following meanings unless indicated otherwise.

"Alkyl" refers to a fully saturated acyclic monovalent radical containing carbon and hydrogen, and which may be cyclic, branched or linear. Examples of alkyl groups are methyl, ethyl, n-butyl, t-butyl, n-heptyl, and isopropyl. Preferably, the alkyl group has one to eight carbon atoms. "Lower alkyl" refers to an alkyl radical of one to six carbon atoms, as exemplified by methyl, ethyl, n-butyl, i-butyl, t-butyl, isoamyl, n-pentyl, and isopentyl, typically one to four carbon atoms.

"Alkenyl" refers to a monovalent or divalent unsaturated, preferably mono-unsaturated, radical containing carbon and hydrogen, and which may be cyclic, branched or linear. Preferably, the alkenyl group has one to eight carbon atoms. "Lower alkenyl" refers to an alkenyl group having one to six, typically one to four, carbon atoms.

"Alkynyl" refers to a monovalent or divalent unsaturated, preferably monounsaturated, radical containing carbon and hydrogen and having at least one carbon-carbon triple bond. Preferably, the alkynyl group has one to eight carbon atoms. "Lower alkynyl" refers to an alkynyl group having one to six, typically one to four, carbon atoms.

"Allenyl" refers to a substituent comprising the moiety —CH=C=CH$_2$.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethyl ammonium, bis(2-hydroxyethyl)ammonium, phenylethylbenzylammonium, dibenzylethylene diammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

For the purposes of the current disclosure, the following numbering scheme is used for triptolide and triptolide derivatives:

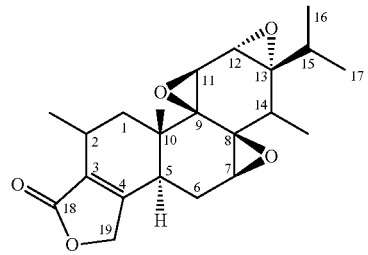

II. Triptolide Derivatives

The compounds of the invention are derivatives of triptolide resulting from alkylation at C2, C14, and/or C16, by addition of a carbon nucleophile to a carbonyl group, as described further herein. The compounds of the invention may be prepared from triptolide, tripdiolide or 16-hydroxytriptolide. Triptolide can be obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for preparing triptolide, tripdiolide and 16-hydroxytriptolide are known in the art and are described, for example, in Kupchan et al. (1972, 1977); Lipsky et al. (1994); Pu et al. (1990); and Ma et al. (1992).

The compounds of the invention are represented by Formula I below:

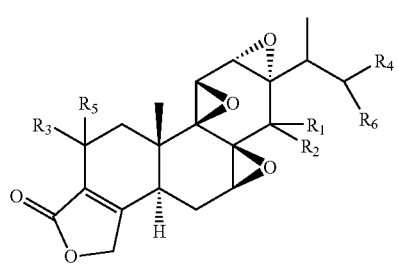

where:
R$^1$ is H or R, where R is selected from lower alkyl, alkenyl, alkynyl, and allenyl, or R$^1$ together with R$^2$=O (oxo);
R$^2$=OH or R$^1$ and R$^2$ together=O (oxo);
CR$^3$R$^5$ and CR$^4$R$^6$ are selected from CH$_2$, CHOH and CROH;
at least one of R$^1$, R$^5$ and R$^6$ is R; and
at least one of CR$^3$R$^5$ and CR$^4$R$^6$ is CH$_2$.

In selected embodiments, R is selected from methyl, allyl, and 2-propynyl; in one embodiment, R is methyl. In one embodiment, which includes C2- or C16-modified triptonides, R$^1$ together with R$^2$=oxo, one of CR$^3$R$^5$ and CR$^4$R$^6$ is CROH, and the other is CH$_2$. In another embodiment, which includes C2- or C16-modified triptolides, R$^1$ is H, R$^2$ is OH, one of CR$^3$R$^5$ and CR$^4$R$^6$ is CROH, and the other is CH$_2$.

In a further embodiment, which includes C14-modified triptolides, R$^1$ is R and R$^2$ is OH. Such a compound may also be modified either at C2 or at C16; in one embodiment, neither of these sites is modified; i.e. each of CR$^3$R$^5$ and CR$^4$R$^6$ is CH$_2$. When R is methyl, this embodiment includes the compound designated herein as PG670.

Preferably, when either $CR^3R^5$ or $CR^4R^6$ is CHOH or CROH, the stereochemistry at C2 or C14, respectively, is such that the hydroxyl group is depicted above the plane of the page.

The compounds of Formula I can be prepared from the known compounds triptolide, tripdiolide, and 16-hydroxytriptolide, by oxidation of one or more hydroxyl groups to keto or aldehyde groups, followed by reaction with a carbon nucleophile, such as an organolithium or organomagnesium halide (Grignard) reagent. Description of oxidizing reagents and processes suitable for selective oxidation of alcohols is provided in references such as M. Hudlicky, *Oxidations in Organic Chemistry* (ACS Monograph Series 186, 1990), R. C. Larock, *Comprehensive Organic Transformations* ($2^{nd}$ Ed., Wiley, 1999), or J. March, *Advanced Organic Chemistry* ($4^{th}$ Ed., Wiley, 1992). Strong acidic or basic conditions should be avoided. If necessary, the desired product is isolated from any side products using, for example, HPLC. Several examples are given below.

In Scheme 1, the secondary alcohol at C14 of triptolide is oxidized to a ketone (known as triptonide) using, for example, chromium trioxide-pyridine complex, $CrO_2Cl_2$/alumina, or comparable oxidizing reagents. Reaction with methyl lithium ($CH_3Li$) yields 14-C-methyl triptolide. Preparation and characterization of this compound is described further in Example 1.

In Scheme 1 above, both stereochemistries at C14 are shown, and in the following Schemes, the stereochemistry at the reaction site is not depicted. However, in reactions in which a chiral center is produced (i.e. additions at C14 and C2), the product resulting from addition "below" the molecule; that is, as in the product on the left in Scheme 1, generally predominates. This product is also shown in Example 1 below.

In Scheme 2, both secondary alcohols of tripdiolide are oxidized to ketones, using an oxidant as described above. Reaction with allyl lithium ($CH_2=CHCH_2Li$) gives both the diol (a), from reaction at both ketones, and the ketol (b), a result of reaction only at the less hindered ketone.

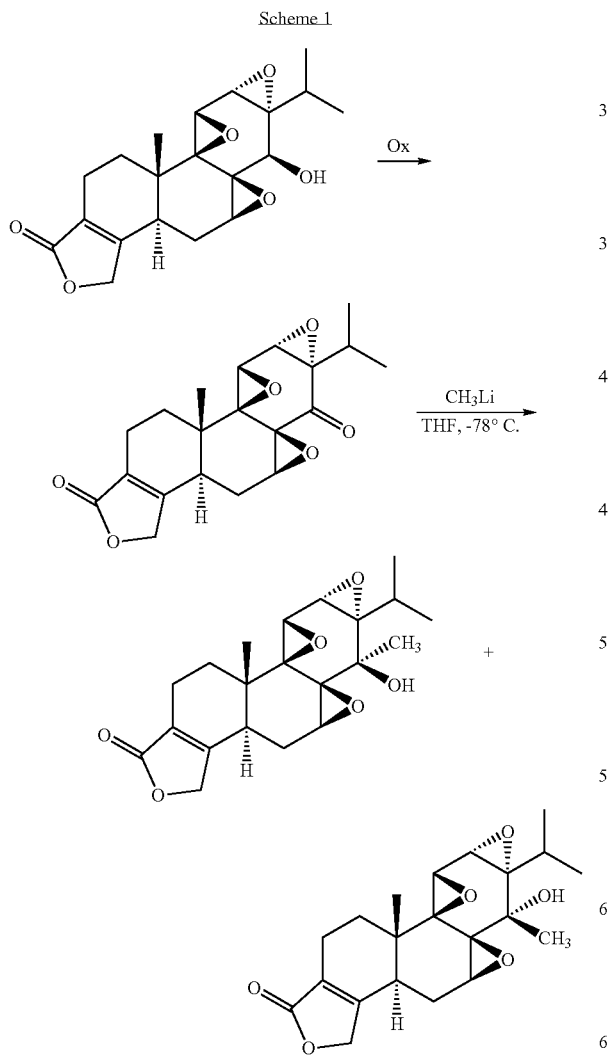

Scheme 1

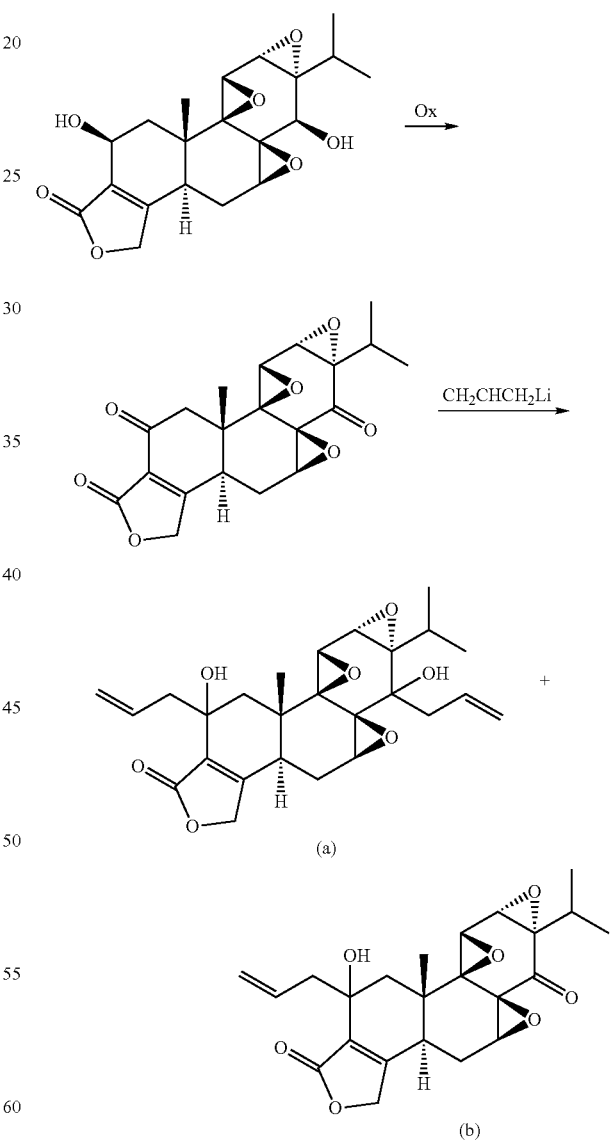

Scheme 2

In Scheme 3, the less hindered alcohol at C2 of tripdiolide is oxidized to the ketone, using a stoichiometric amount of a reagent such as those noted above, under mild conditions. Reaction with allyl lithium gives the tertiary alcohol at C2.

Scheme 3

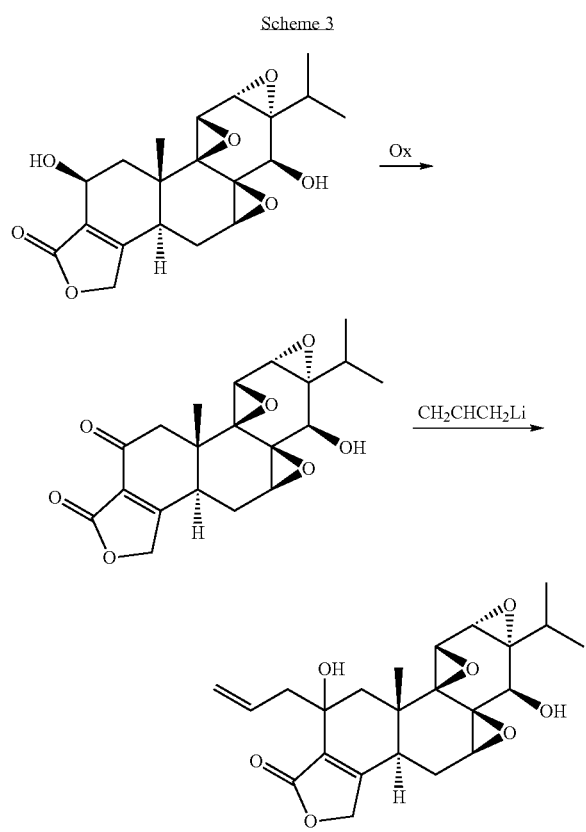

In Scheme 4, the secondary and primary alcohols of 16-hydroxy triptolide are oxidized with a reagent that will not further oxidize the product aldehyde, e.g. DMSO, pyridinium chlorochromate (Corey' reagent), or ceric ammonium nitrate, to give the keto-aldehyde intermediate. This compound is reacted with 2-propynyl lithium (CH≡CCH$_2$Li) to give both the diol (c) and the ketol (d), a result of reaction only at the less hindered aldehyde.

Scheme 4

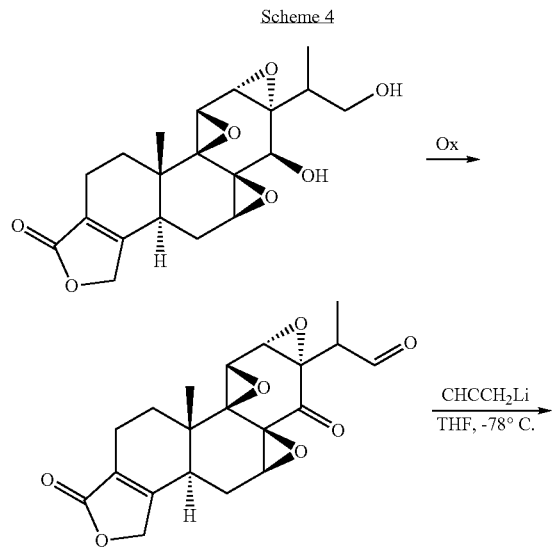

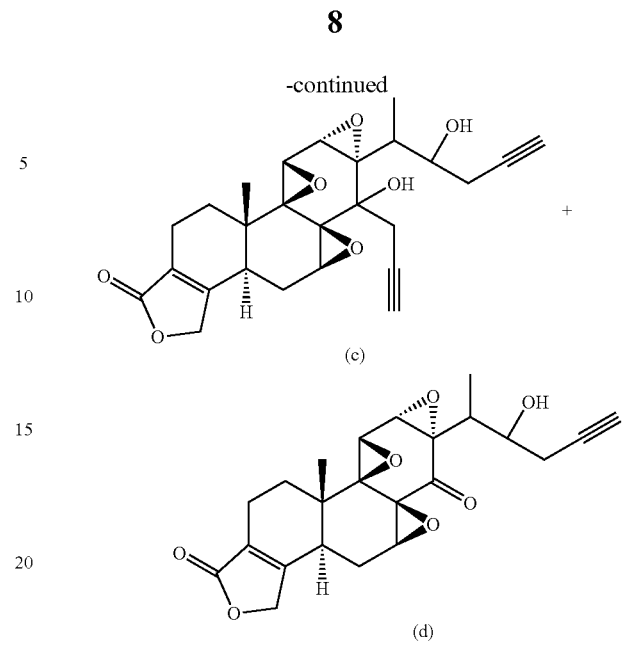

In Scheme 5, only the primary alcohol of 16-hydroxy triptolide is oxidized, using a selective oxidizing agent such as, for example, RuCl$_2$(PPh$_3$)$_3$; (Me$_3$SiO)$_2$/catalytic RuCl$_2$(PPh$_3$)$_3$; DMSO/ClCOCOCl/Et$_3$N; or DMSO/pyridine-SO$_3$/i-Pr$_2$NEt (see Larock, cited above). Reaction with 2-propynyl lithium gives the diol as shown.

Scheme 5

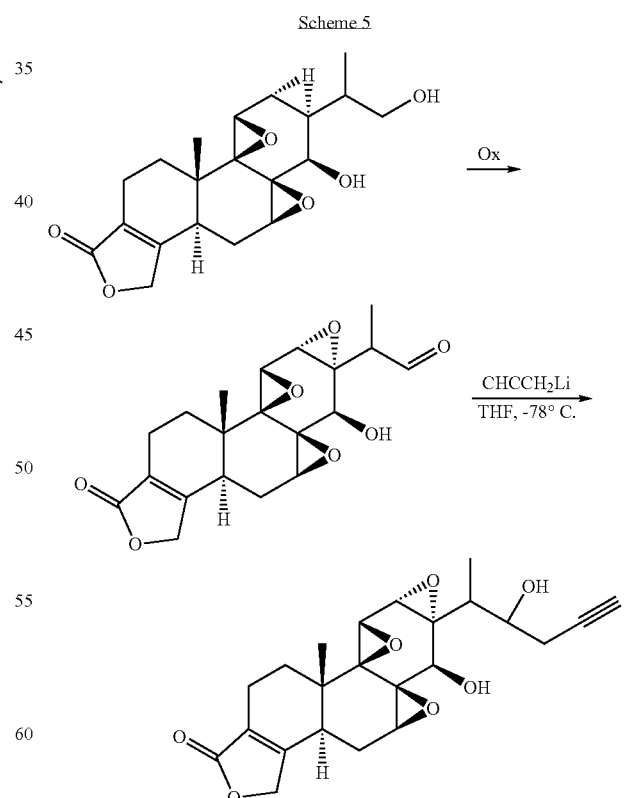

As shown in Scheme 6, below, reaction (of triptonide, in this case) with the organometallic 2-propynyl reagents can also produce the rearranged allenyl product.

Scheme 6

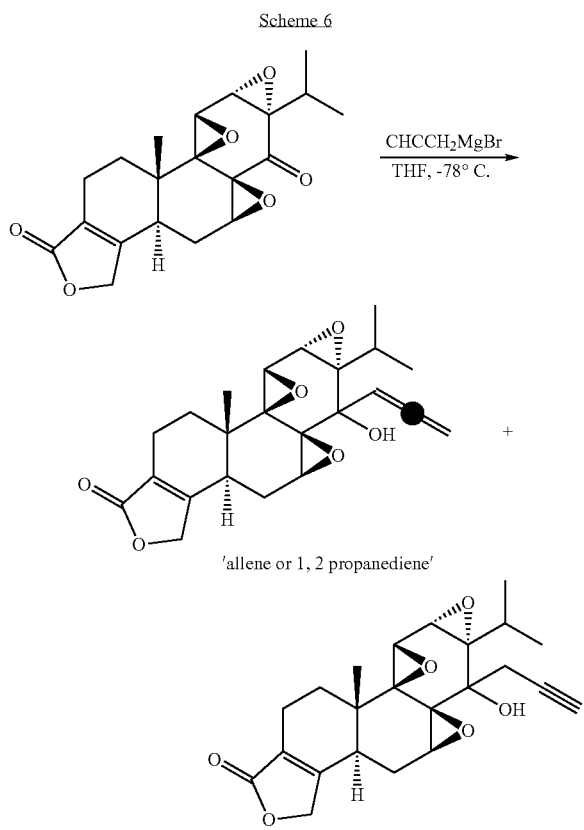

'allene or 1, 2 propanediene'

The methods described herein may also be used for preparation of isotopically labeled compounds, by employing $^{14}C$-containing carbon nucleophiles.

III. Therapeutic Compositions

Formulations containing the triptolide derivatives of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifyng agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide derivative in a suitable intravenous solution, such as sterile physiological salt solution.

Liquid compositions can be prepared by dissolving or dispersing the triptolide derivative (about 0.5% to about 20%) and optional pharmaceutical adjuvants in a pharmaceutically acceptable carrier, such as, for example, aqueous saline, aqueous dextrose, glycerol, or ethanol, to form a solution or suspension. The high water solubility of the compounds of the invention make them particularly advantageous for administering in aqueous solution, e.g. by intraperitoneal injection. Although aqueous solutions are preferred, compositions in accordance with the invention may also be formulated as a suspension in a lipid (e.g., a triglyceride, a phospholipid, or a polyethoxylated castor oil such as "CREMOPHOR EL™"), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in an effective amount for effecting immunosuppression in a subject or apoptosis in a targeted cell.

As described, for example, in Panchagnula et al. (2000), the partition coefficient or logP of a pharmaceutical agent can affect its suitability for various routes of administration, including oral bioavailability. The compounds described herein have higher calculated logP values than the parent compound, triptolide (see Table), making them better candidates for oral availability. (Compounds represented in the Table are compounds of formula I where $R^2$ is OH, $CR^3R^5$ and $CR^4R^6$ are both $CH_2$, and $R^1$ is as indicated. As described above, the stereochemistry at C14 in these compounds is such that the hydroxyl group is depicted above the plane of the page.)

| Compounds | LogP[a] | LogP[b] |
|---|---|---|
| Triptolide ($R^1$ = H) | −0.08 | 0.27 |
| $R^1$ = —$CH_3$ (PG670) | 0.14 | 0.34 |
| $R^1$ = —CH=C=$CH_2$ | 0.63 | 0.89 |
| $R^1$ = —$CH_2$CH=CH | 0.77 | 0.99 |
| $R^1$ = —$CH_2$—C≡CH | 0.30 | 0.53 |
| $R^1$ = —C≡CH | 0.02 | 0.28 |
| $R^1$ = —CH=$CH_2$ | 0.49 | 0.74 |
| $R^1$ = —$(CH_2)_5CH_3$ | 2.30 | 2.40 |

[a]calculated per A. K. Ghose et al., J. Chem. Inf. Comput. Sci. 27: 21–35 (1987); SD = 0.47
[b]calculated per V. N. Viswanadhan, J. Chem. Inf. Comput. Sci. 29: 163 (1989); SD = 0.49

IV. Immunomodulating and Antiinflammatory Treatment

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The compositions of the present invention are useful in applications for which triptolide and its prodrugs and other derivatives have proven effective, e.g. in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. Triptolide and the present derivatives are also useful for treatment of other inflammatory conditions, such as traumatic inflammation, and in reducing male fertility.

The method is useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The method is also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

In another aspect, the invention includes a method of treatment or prevention of graft-versus-host disease, resulting from transplantation into a recipient of matched or mismatched bone marrow, spleen cells, fetal tissue, cord blood, or mobilized or otherwise harvested stem cells. The dose is preferably in the range 0.25–2 mg/kg body weight/day, preferably 0.5–1 mg/kg/day, given orally or parenterally.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, and various allergies. In treating an autoimmune condition, the patient is given the composition on a periodic basis, e.g., 1–2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1–25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

Also within the scope of the invention is a combination therapy comprising a compound of formula I and one or more conventional immunosuppressive agents. These immunosuppressant agents within the scope of this invention include, but are not limited to, IMUREK™ (azathioprine sodium), brequinar sodium, SPANIDIN™ (gusperimus trihydrochloride, also known as deoxyspergualin), mizoribine (also known as bredinin), CELLCEPT™ (mycophenolate mofetil), NEORAL™ (Cyclosporin A; also marketed as a different formulation under the trademark SAN-DIMMUNE™), PROGRAF™ (tacrolimus, also known as FK-506), RAPIMMUNE™ (sirolimus, also known as rapamycin), leflunomide (also known as HWA-486), ZENAPAX™, glucocortcoids, such as prednisolone and its derivatives, antibodies such as orthoclone (OKT3), and antithymyocyte globulins, such as thymoglobulins. The compounds are useful as potentiators when administered concurrently with another immunosuppressive drug for immunosuppressive treatments as discussed above. A conventional immunosuppressant drug, such as those above, may thus be administered in an amount substantially less (e.g. 20% to 50% of the standard dose) than when the compound is administered alone. Alternatively, the triptolide derivative and immunosuppresive drug are administered in amounts such that the resultant immunosuppression is greater than what would be expected or obtained from the sum of the effects obtained with the drug and triptolide derivative used alone. Typically, the immunosuppressive drug and potentiator are administered at regular intervals over a time period of at least 2 weeks.

The compositions and method of the invention are also useful for the treatment of inflammatory conditions such as asthma, both intrinsic and extrinsic manifestations. For treatment of asthma, the composition is preferably administered via inhalation, but any conventional route of administration may be useful. The composition and method may also be used for treatment of other inflammatory conditions, including traumatic inflammation, inflammation in Lyme disease, psoriasis, chronic bronchitis (chronic infective lung disease), chronic sinusitis, sepsis associated acute respiratory distress syndrome, Behcet's disease, pulmonary sarcoidosis, pemphigus, pemphigoid inflammatory bowel disease, and ulcerative colitis.

The compositions of the invention may also be administered in combination with a conventional anti-inflammatory drug (or drugs), where the drug or amount of drug administered is, by itself, ineffective to induce the appropriate suppression or inhibition of inflammation.

The dose that is administered is preferably in the range of 1–25 mg/kg patient body weight per day, with lower amounts being preferred for parenteral administration, and higher amounts being preferred for oral administration. Optimum dosages can be determined by routine experimentation according to methods known in the art.

V. Anticancer Treatment

Triptolide derivatives have shown effectiveness in cancer treatment. See, for example, co-owned U.S. Pat. No. 6,620,843, incorporated herein by reference, which describes high efficacy of a triptolide derivative, in comparison to 5-FU and CPT-11, in inhibiting tumor growth in studies with tumor xenografts of the HT-29 human colon cancer cell line. The triptolide derivative (triptolide 14-succinate) strongly inhibited tumor growth, to a significantly greater degree than 5-FU and CPT-11, and induced tumor regression.

The invention thus includes the use of compositions as described above to treat cancers, including cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin and gastrointestinal tract), solid organs, the nervous system, and musculo-skeletal tissue. The triptolide derivatives may be used for treatment of various cancer cell types, including, but not limited to, breast, colon, small cell lung, large cell lung, prostate, malignant melanoma, liver, kidney, pancreatic, esophogeal, stomach, ovarian, cervical or lymphoma tumors. Treatment of breast, colon, lung, and prostate tumors is particularly contemplated. Treatment of leukemias is also contemplated. The composition may be administered to a patient afflicted with cancer and/or leukemia by any conventional route of administration, as discussed above.

The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

EXAMPLES

The following examples are intended to illustrate but not in any way limit the invention.

Example 1

Preparation of 14-C-methyltriptolide (PG670)

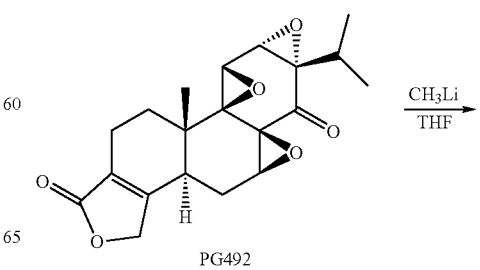

PG492

-continued

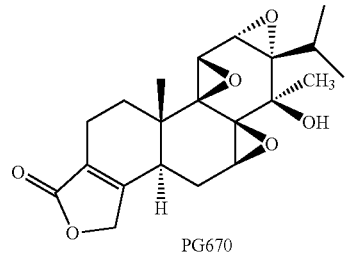

PG670

To a solution of triptonide, PG492 (60 mg, 0.17 mmol) in THF (5 ml) at −78° C. was added 0.45 ml of methyl lithium (1.4 M solution in ethyl ether, 0.63 mmol, 3.7 eq) under $N_2$. The solution was stirred at −78° C. for 2 hrs. 45 mins. and then at room temperature for 2 hrs., at which time the starting material had disappeared on TLC. Acetic acid (1 ml) was slowly added. The solution was then concentrated under vacuum. The crude product was dissolved in dichloromethane (3 ml) and passed through a pad of silica gel, which was then washed with 5% methanol in ethyl acetate (80 ml). After removal of solvent, 78 mg of crude product was obtained. This was dissolved in acetonitrile (0.6 ml) and filtered. The product mixture was separated on BPLC, using a 10×250 mm column of Econosil C18 (5μ) and a guard column cartridge (7.5×4.6 mm) of Alltima C18 (5μ), both from Alltech, with mobile phase $CH_3CN/H_2O$ 40/60 with a flow rate of 2.0 ml/min. The sixth peak, having a retention time of 32.13 mins., was collected and concentrated under vacuum. The product had m/z 374 (7.9 mg, yield: 12.6%).

The structure was verified by NMR. $H^1$ NMR (300 MHz, $CDCl_3$): δ=4.68 (2H, s, 19-$CH_2$), 3.95 (1H, d, 11-CH), 3.50 (1H, d, 12-CH), 3.49 (1H, s, 14-OH), 3.39 (1H, d, 7-CH), 2.69 (1H, m, 5-CH), 2.46 (1H, m, 15-CH), 2.33 (1H, m, 2-CHb), 2.12 (1H, m, 1-CHa), 1.14 (3H, s, 14-$CH_3$ or 20-$CH_3$), 1.09 (3H, d, 17-$CH_3$), 1.08 (3H, s, 20-$CH_3$ or 14-$CH_3$), 0.81 (3H, d, 16-$CH_3$) ppm.

Example 2

Apoptosis Assays

A. Incubation of Compounds with Human Serum

Pooled human serum was stored in aliquots at −80° C. Test compounds were added at 20 mM to thawed human serum in 1.5 ml microfuge tubes and incubated at 37° C. in a water bath for 48 hours. The test samples were placed on ice until dilution for the bioassay. Controls consisted of the compounds incubated in complete tissue culture medium (RPMI 1640 medium plus 5% heat-inactivated fetal calf serum, 1% HEPES, 1% pen/strep, 1% glutamine) rather than human serum.

B. Annexin V Apoptosis Assay.

Test samples (incubated in human serum as described in section A) were diluted to 1 mM in complete tissue culture medium. Aliquots were placed in microculture plates and serial dilutions were prepared so that the final concentration would encompass the range of 2 to 6,000 nM with half-log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of $1\times10^6$ cells/ml. A volume of 100 μl of Jurkat cells ($1\times10^5$ cells) was added to wells containing 100 μl of the diluted compounds, and the plates were incubated at 37° C. in a 5% $CO_2$ incubator.

After 24 hours, the plates were centrifuged to pellet the cells, and the cells were washed twice with 2% heat-inactivated fetal calf serum in PBS. To each well, 500 ul of binding buffer was added, according to the Annexin V assay procedure (BioVision, Inc., Mountain View, Calif.). Next, 5 μl of the fluorescein isothiocyanate (FITC) conjugate of Annexin V (BioVision, Inc.) was added to each well, followed by 5 minutes of incubation in the dark. In some assays, propidium iodide (BioVision, Inc.) was added at this stage to check for necrotic cells. The contents of the wells were individually transferred into test tubes, and apoptosis was analyzed using a FACSCalibur flow cytometer (BD Immunocytometry Systems, San Jose, Calif.). Cells positive for Annexin V binding were considered to be apoptotic, and the data were calculated as percent apoptotic cells.

Data were plotted as the concentration of compound incubated in serum versus percent apoptotic cells. The results for PG670 (14-methyl triptolide), compared with PG490 (triptolide) and solvent controls, are given in FIG. 1.

C. Terminal Deoxynucleotidyl Transferase Apoptosis Assay

In this assay, test samples are prepared as described in section A above and diluted as described in section B. Jurkat human T lymphocyte cells are added, also as described in section B, and the plates are incubated at 37° C. in a 5% $CO_2$ incubator. After 24 hours, the plates are centrifuged to pellet the cells, and the cells are washed with PBS. The cells are fixed in paraformaldehyde, washed, treated with ethanol, washed and then incubated with the enzyme terminal deoxynucleotidyl transferase (TdT) and fluorescein labeled-deoxyuridine (dUTP). The process allows 3' end labeling of DNA molecules nicked during the DNA fragmentation phase of apoptosis (terminal deoxynucleotidyl transferase dUTP nick end labeling; TUNEL labeling). The cells are washed, treated with ribonuclease, washed and resuspended in medium containing propidium iodide to distinguish intact apoptotic cells. The contents of the assay wells are individually transferred into test tubes, and apoptosis levels are analyzed using a FACSCalibur flow cytometer (BD Immunocytometry Systems, San Jose, Calif.). Cells positive for Fl-dUTP are considered to be apoptotic.

Example 3

IL-2 Production Assay

Test samples, incubated in human serum as described in Example 2A, were diluted to 1 mM in complete tissue culture medium. Aliquots were placed in microculture plates that had been coated with anti-CD3 antibody (used to stimulate the production of IL-2 by Jurkat cells), and serial dilutions were prepared so that the final concentration would encompass the range of 0.001 to 10,000 nM in log increments. Cells from an exponentially expanding culture of the Jurkat human T lymphocyte cell line (#TIB-152 obtained from American Type Culture Collection, Manassas, Va.) were harvested, washed once by centrifugation and dilution in complete tissue culture medium, and diluted to a concentration of $2\times10^6$ cells/ml. A volume of 50 μl of Jurkat cells ($1\times10^5$ cells) was added to wells containing 100 μl of the diluted compounds, 50 μl of PMA (10 ng/ml) was added to each well, and the plates were incubated at 37° C. in a 5% $CO_2$ incubator. After 24 hours, the plates were centrifuged to pellet the cells, 150 μl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody. The data were expressed as ng/ml of IL-2.

Figure 2:
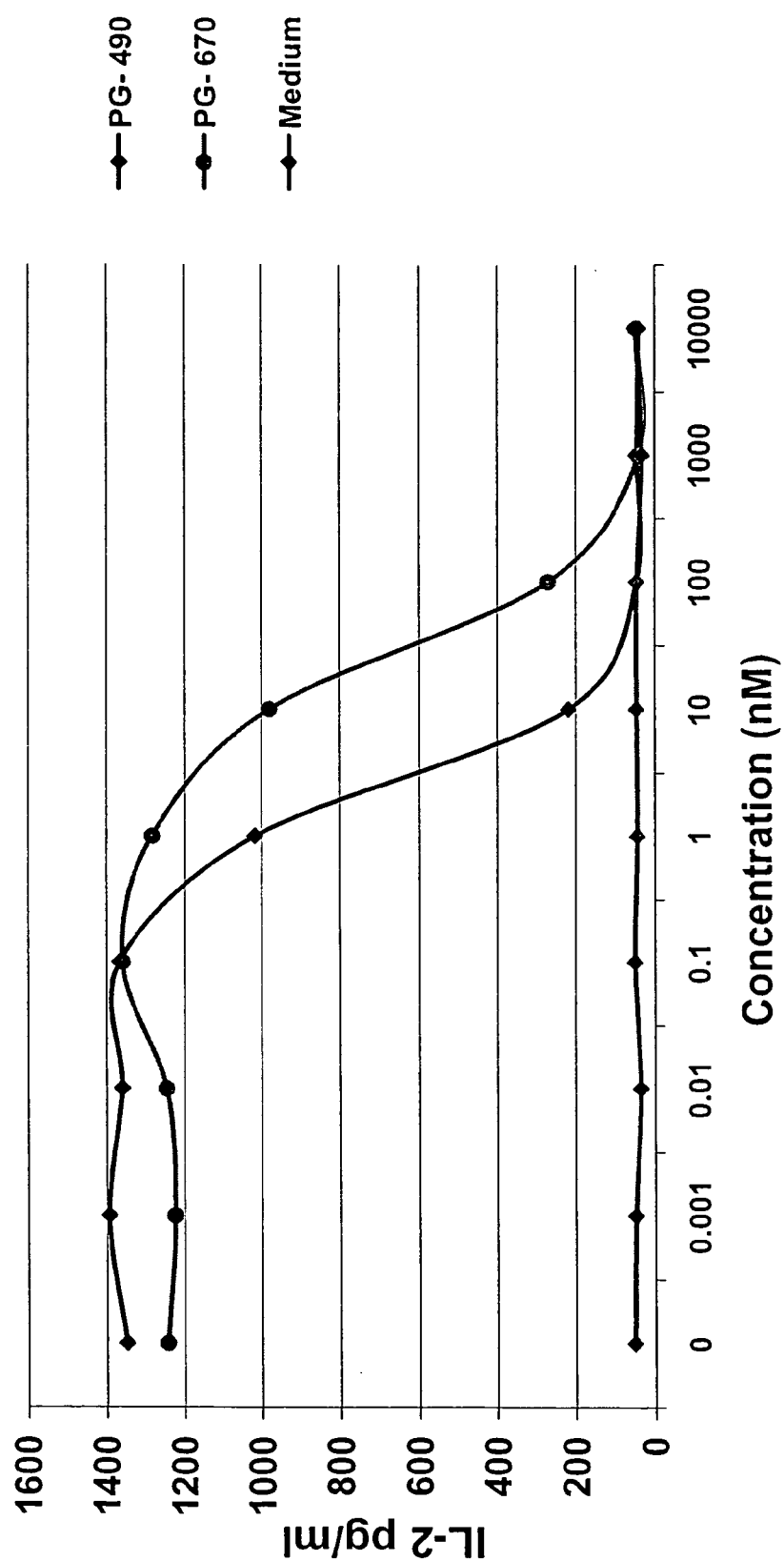
FIG. 2 shows inhibition of IL-2 production in Jurkat cells by a compound of the invention (PG670), in comparison with triptolide (Example 3).

The data were plotted as the concentration of compound incubated in serum versus IL-2 concentration. The results for PG670 (14-methyl triptolide), compared with PG490 (triptolide) and a solvent control, are given in FIG. 2.

It is claimed:

1. A compound having the structure I:

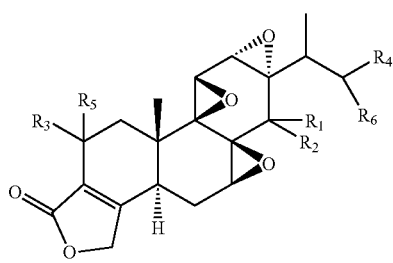

where:
R$^1$ is H or R, where R is selected from lower alkyl, alkenyl, alkynyl, and allenyl, or R$^1$ together with R$^2$=O (oxo);
R$^2$=OH or R$^1$ and R$^2$ together=O (oxo);
CR$^3$R$^5$ and CR$^4$R$^6$ are selected from CH$_2$, CHOH and CROH;
at least one of R$^1$, R$^5$ and R$^6$ is R; and
at least one of CR$^3$R$^5$ and CR$^{46}$ is CH$_2$.

2. The compound of claim 1, wherein R is selected from methyl, allyl, and 2-propynyl.

3. The compound of claim 2, wherein R is methyl.

4. The compound of claim 1, wherein R$^1$ together with R$^2$=oxo, one of CR$^3$R$^5$ and CR$^{46}$ is CROH, and the other is CH$_2$.

5. The compound of claim 1, wherein R$^1$ is H, R$^2$ is OH, one of CR$^3$R$^5$ and CR$^4$R$^6$ is CROH, and the other is CH$_2$.

6. The compound of claim 1, wherein R$^1$ is R and R$^2$ is OH.

7. The compound of claim 6, wherein each of CR$^3$R$^5$ and CR$^4$R$^6$ is CH$_2$.

8. The compound of claim 7, wherein R is methyl.

* * * * *

UNITED STATES PATENT AND TRADEMARK OFFICE
CERTIFICATE OF CORRECTION

PATENT NO. : 7,019,151 B2 Page 1 of 1
APPLICATION NO. : 10/738753
DATED : March 28, 2006
INVENTOR(S) : Dongcheng Dai and John H. Musser It is certified that error appears in the above-identified patent and that said Letters Patent is hereby corrected as shown below:

In column 18, line 10, that portion of the claim reading "$CR^{46}$" should read "$CR^4R^6$".

In column 18, line 15, that portion of the claim reading "$CR^{46}$" should read "$CR^4R^6$".

Signed and Sealed this

Fifteenth Day of August, 2006

JON W. DUDAS
*Director of the United States Patent and Trademark Office*